United States Patent [19]

Wolff

[11] Patent Number: 5,028,138

[45] Date of Patent: Jul. 2, 1991

[54] METHOD OF AND APPARATUS FOR OBTAINING OBJECT DATA BY MACHINE VISION FORM POLARIZATION INFORMATION

[76] Inventor: Lawrence B. Wolff, 265 E. 66 St., Apt. 41B, New York, N.Y. 10021

[21] Appl. No.: 355,657

[22] Filed: May 23, 1989

[51] Int. Cl.$^5$ .............................................. G01J 4/00
[52] U.S. Cl. ...................................... 356/369; 358/364
[58] Field of Search ............................... 356/364–370, 356/376; 250/225

[56] References Cited

U.S. PATENT DOCUMENTS

| | | | |
|---|---|---|---|
| 4,030,836 | 6/1977 | Smith | 356/369 |
| 4,695,163 | 9/1987 | Schachar | 356/369 |
| 4,741,621 | 5/1988 | Taft et al. | 356/376 |

*Primary Examiner*—Richard A. Rosenberger
*Assistant Examiner*—Hoa Pham
*Attorney, Agent, or Firm*—Jones, Tullar & Cooper

[57] ABSTRACT

A method and apparatus for determining object characteristics such as shape and relative electrical conductivity and for resolving specular and diffuse components of reflection are disclosed. These object characteristics are determined by measuring the following polarization parameters of reflected light from the object surface: (i) the magnitude of the minimum polarization component, (ii) the magnitude of the maximum polarization component, and (ii) the directional orientation of the minimum polarization component. These parameters are used to ascertain at an object point the specular plane and the ratio of the Fresnel reflection coefficients, perpendicular to parallel, with respect to the specular plane. Both of these are used for the determination of the surface normal at object points. The numerical value of the Fresnel reflection coefficient is used to discriminate between surfaces of varying electrical conductivity, lower values indicating highly conductive metals, higher values indicating poorly conducting dielectrics. The numerical value of the Fresnel reflection coefficient is used to resolve specular and diffuse reflection components.

20 Claims, 9 Drawing Sheets

METHOD OF AND APPARATUS FOR OBTAINING OBJECT DATA BY MACHINE VISION FORM POLARIZATION INFORMATION

TECHNICAL FIELD

This invention relates mostly to machine vision applications. It can be applied to, but certainly not limited to, automatic part inspection. It can be useful for any automated robotic application requiring the visual information supplied by the invention. The method can also be adapted to applications in aerial reconnaissance and remote sensing.

BACKGROUND OF THE INVENTION

There has been increasing motivation for obtaining visual object data from physical modeling of the image formation process. Most existing vision methods utilize heuristic techniques on image gray values that are based primarily on image properties that ignore the image formation process. These methods are developed largely on a trial and error basis and are made to work in very domain specific environments. These heuristic methods break down very easily upon small deviations from their specifically intended domain.

Vision methods which are primarily based on physical laws are more robust in the sense that their behavior is determined by well defined physical assumptions. The area of physical modeling of image formation pertaining to this invention is called "radiometric modeling". Radiometric modeling usually involves three components; (i) an illumination model, (e.g., incident orientation and incident intensity of light sources), (ii) a reflectance model for objects in the scene (e.g., Lambertian model), and, (iii) camera sensor model that relates gray value representation at a pixel to the actual radiance that is incident at that pixel. Most existing machine vision methods that utilize radiometric modeling compute local surface normal information (i.e., 3-D shape information) on smooth object surfaces. These methods are important particularly for smooth featureless surfaces because stereo triangulation techniques are inadequate due to the lack of features (e.g., edges) for depth computation.

Given a reflectance model for an object surface expressing reflected radiance as a function of surface orientation and other imaging parameters, a sensed reflected radiance value constrains the local surface orientation at the corresponding point to be on a specific locus of surface orientation values. Photometric stereo, when applied to diffuse reflecting surfaces, is a radiometric vision method which disambiguates this surface orientation locus by taking additional sensed reflected radiance values from the same object point for different incident light source orientations. For a simple Lambertian reflectance model surface, only three different noncoplanar incident light source orientations are required to uniquely ascertain local surface orientation. Both point light sources and extended light sources can be utilized.

For highly specular reflecting surfaces, such as metals, implementation of photometric stereo involves the use of extended structured light sources, or a vast array of many different point light sources. This is so as to produce specular reflection from many different possible surface orientations. Determining surface orientation for specular surfaces involves the simple geometry of specular reflection as the reflectance model. Clearly for specular reflection the angle of incidence equals the angle of reflection with respect to the surface normal. If the incident orientation of a lighting element is known relative to the viewing vector of the camera sensor, the normal at the object point specularly reflecting the light received from the lighting element is simply the bisector of the incident light vector and the viewing vector. The major problem to be solved in this implementation of photometric stereo for specular surfaces is the correspondence between specularly reflecting light perceived by the camera sensor at an object point, and the lighting element that produced it. Using and extended light source this is accomplished by placing on the light source multiple, calibrated intensity gradient filters. Multiple images are taken each for a different filter placed on the extended source, and various ratios of sensed specularly reflected radiance from an object point correspond to the calibrated incident orientation of the correct lighting element. Using a vast array of point light sources (e.g., a hemispherical array of thin optic fibers), multiple images are taken while different known subsets of the point light sources are turned on and off. From these multiple images, the on-off sequence for a particular point specular reflection from the object surface uniquely determines the actual point light source from which it was produced. Usually a binary encoding scheme for the light sources is employed to reduce the number of multiple images needed.

In all photometric stereo implementations the camera sensor always remains static between multiple images. Therefore there is no correspondence problem between pixels. However, photometric stereo does require the precise calibration of the incident orientation of multiple light sources, or the calibration of a single light source multiple times as it is moved into different incident orientations. Usually empirical look-up tables for reflectance as a function of surface orientation are computed for each different diffuse surface used. These tables however are very sensitive to typical changes in light source emitted radiance over time. Photometric stereo is generally not applied to "hybrid" regions of an object surface where both diffuse and specular components of reflection are significant. Another big limitation of photometric stereo is that the camera sensor is restricted to an orthographic field of view. Afterall, the calibration of the incident orientation of a light source is only applicable to a small region of space that an object can occupy. The incident orientation for a given light source may be extremely variable throughout a wide perspective field of view unless the light source is very far away.

Some limited results have been reported using radiometric modeling to separate out diffuse and specular reflection components, based on color analysis. This work is limited to inhomogeneous dielectrics such as plastics and rubber. On inhomogeneous dielectrics the specular component of reflection is the same color as the illuminating light source. If this color is distinct from the intrinsic color of the inhomogeneous dielectric (i.e., the color of the diffuse component) then color analysis can quantitatively separate out the two reflection components. If the color of the light source is unknown, heuristic segmentation procedures need to be invoked to determine the color of the light source.

The only known use of polarizing filters in machine vision is to visually suppress strong specular regions using the method of "cross polorization". Cross polarization is a method whereby a linear polarizing filter is placed over the illuminating light source as well as over the camera sensor. The orientations of these two polarizers are 90° with respect to one another so that the reflecting specular glare off of an object surface gets canceled out. The use of polarizers in machine vision has only been known to improve image quality rather than used to extract physical information from an object scene.

No machine vision method is known whatsoever that can classify an object surface as being metal or dielectric.

SUMMARY OF THE INVENTION

The invention disclosed herein using polarization information has distinct advantages over the background art in obtaining the individual object data mentioned above.

A severe limitation of existing radiometric vision methods in determining local surface normals is that the camera sensor is restricted to orthographic viewing. This is due to the fact that existing radiometric methods rely upon reflectance information which is dependent upon incident light source orientation. The method and apparatus disclosed herein does not require any knowledge whatsoever of the incident orientation of a light source to compute local surface normals. Hence, local surface normals can be computed on objects in perspective fields of view without any calibration of the incident orientation of the light source. Also the light source used for the disclosed method can be of much cruder quality than normally implemented for photometric stereo as long as the emitted radiance from the light source does not vary significantly within a time period of a few minutes. The method disclosed is also generally more passive than photometric stereo methods which require either the flashing on and off of different light sources, or the movement of a single light source. The passive nature of the disclosed method combined with the lack of need for calibrated incident orientations of light sources makes the domain of application larger than just the very controlled environment of typical machine vision applications. The sun itself can be used as a light source for the determination of surface normals and dielectric/metal classification in aerial reconnaissance and remote sensing.

The method and apparatus disclosed herein separate diffuse and specular components of reflection on all material surfaces. That, is the method is not restricted to the same domain as the background art to inhomogeneous dielectrics. Since the method is based on polarization information, the separation of reflection components is independent of the variable color properties of the light source and object. Also the method disclosed herein can separate specular and diffuse components produced from multiple interobject reflections that would normally confuse the existing method(s) of the background art.

The basic premise upon which this invention is built is that the polarization state of specularly reflected light from object surfaces gives crucial physical information about the object surface which is very useful for many machine vision applications. This invention therefore incorporates polarization into the radiometric model. Most typical light sources emit completely upolarized light radiation and unless otherwise stated, the illuminating light source will always be assumed to be unpolarized. The polarization state of reflected light from object surfaces can be analyzed by transmitting the reflected light through a linear polarizer, at various orientations, before being sensed by a camera device which records the transmitted radiance through the polarizer. The transmitted radiance through a linear polarizer, at a given orientation of the polarizer, resolves the polarization component of the reflected light in this orientation.

Specular reflection of light rays occurs at purely planar interfaces, larger in dimension than the wavelength of incident light, between the material surface and the surrounding air. The polarization state of specularly reflected light is determined by the Fresnel reflection coefficients for the material surface. The diffuse reflection component which arises from other reflection phenomena such as temporary penetration into the outer surface layer, multiple specular reflections, diffraction off of features smaller than the incident light wavelength, etc. . . , is assumed to be completely unpolarized.

The analysis of a significant specular reflection component is essential to the functioning of the disclosed method at an object point. Hence the implementation of the method is best performed with an extended light source which maximizes the number of object points in the scene from which the camera sensor receives a significant specular component of reflection. This extended light source need not be special in any way, just as long as variations in emitted radiance from local lighting areas are not significant during the brief time period (maximum a few minutes, if not much less) it takes for producing multiple images corresponding to different orientations of the polarizer in front of the camera sensor. No calibration is required of the light source, as for photometric stereo techniques. For the dielectric/metal material classification part of the method to work, it is necessary that the specular phase angle (defined as the angle between the incident orientation of a specularly reflecting light ray and the reflected orientation of its specular reflection) be restricted to the range from 80° and 140°. No other restrictive imaging geometric assumptions apply to other parts of the method (i.e., for quantitative separation of diffuse and specular reflection components, and, for determination of local surface normals).

The method disclosed depends upon the empirical computation of two quantities, determined for each pixel in the image plane corresponding to an object point. All object data is derived from these two quantities; (i) the "specular plane of incidence", and, (ii) the determination of the "polarization Fresnel ratio". From here on it will be assumed that the image pixels analyzed corresponding to object points, receive a significant amount of specular component of reflection (i.e., the ratio of the specular component to the diffuse component exceeds the reciprocal of the signal-to-noise ratio of the camera sensor).

The specular plane of incidence, relative to a pixel in the image plane corresponding to an object point, is the plane in which specular reflection occurs at that object point into the pixel sensor. This plane is determined by the incident light ray orientation and its subsequent specular reflected orientation into the pixel sensor. For smooth surfaces, the specular plane of incidence contains the local surface normal at the specularly reflecting object point. For a rough surface illuminated by an extended light source, specular reflection into a pixel sensor can occur from an object point along numerous specular planes of incidence. This is because the object point on a rough surface can consist of a multitude of different planar crystalline microfacets with various orientations. The disclosed method is applicable to rough surfaces for which the majority of the specular component of reflection occurs through the specular plane of incidence containing the local surface normal. This is true for many common rough surfaces (e.g., brushed metals).

The "polarization Fresnel ratio" (hereafter referred to as PFR) is the quantity $F_\perp/F_\parallel$ where $F_\perp$ and $F_\parallel$ are the Fresnel reflection coefficients for the object surface material, for the perpendicular and parallel polarization components, respectively. These parallel and perpendicular components of polarization are relative to the specular plane of incidence containing the local surface normal. The Fresnel reflection coefficients are functions of the index of refraction for the material surface, and the specular angle of incidence (defined as the angle between the direction of incidence of a specularly reflecting light ray and the local surface normal; i.e., the specular angle of incidence is half the specular phase angle). The PFR at a pixel uniquely describes the polarization state of the specular reflection component at that pixel.

The specular plane of incidence at a pixel is derived from the orientation of ts linear projection at the camera sensor and the focal point of the camera sensor (i.e., a plane is uniquely determined by a line and a point). Two techniques are disclosed for deriving the orientation of the specular plane of incidence for each image pixel corresponding to an object point. The first technique involves taking transmitted radiance values over a variety of polarizer orientations throughout a range of 90°. The polarizer orientation corresponding to a local minimum transmitted radiance is parallel to the specular plane of incidence, and the polarizer orientation corresponding to a local maximum transmitted radiance is perpendicular to the specular plane of incidence. The second disclosed technique requires transmitted radiance values from only three orientations of the polarizer. The determination of the specular plane of incidence for each pixel corresponding to an object point occurs concurrently from the same set of polarizer orientations for both of the disclosed techniques. Both of these techniques do not require any knowledge of the incident orientation of specularly reflecting light rays from the extended source. Under the assumption that the specular plane of incidence contains the local surface normal, polarization information provides a natural constraint mechanism on local surface normals without using incident orientation light source information. This frees vision methods that utilize radiometric modeling from the restriction of orthographic viewing. A specular plane of incidence can be determined for each pixel corresponding to an object point in a perspective view, constraining that normal to be contained somewhere within this plane.

Using two camera sensors, if the specular plane of incidence is derived for a pixel for each of the camera sensors which correspond to the same object point, the specular planes of incidence can be intersected to uniquely compute the local surface normal at that object point. The two pixels between the two camera sensors do not necessarily have to correspond to exactly the same point, only to object points with the same local surface normal such as any two points on a flat surface.

Using a single camera sensor, local surface orientation can be determined at an object point corresponding to a given pixel, by first computing the specular plane of incidence, and then computing the specular angle of incidence, obtained from determination of the PFR at that object point. It will be shown that there is a functional relationship between the PFR and the specular angle of incidence. Determining local surface normals from a single camera sensor requires that the PFR as a function of specular angle of incidence be calibrated for known surface materials, and that object points be associated with the correct surface material.

Two different techniques will be disclosed for determining the PFR at a pixel corresponding to an object point. As with the determination of the specular plane of incidence, the techniques for determining the PFR at a pixel utilize multiple images corresponding to different polarizer orientations in front of the camera sensor. The first technique approximates the PFR at a pixel by the ratio of the perpendicular to the parallel polarization component of reflected light (polarization components are with respect to the specular plane of incidence). This works well when the specular component of reflection is much greater than the diffuse component of reflection. The second technique is a global technique and assumes that the light source is not very extended. It involves deriving the PFR for a global set of pixels from the slope of linear clusters of points in a polarization space spanned by two axes representing parallel and perpendicular components of polarization.

Determination of the PFR at a pixel always requires that the specular plane of incidence be known, since $F_\perp/F_\parallel$ always refers to polarization components relative to the specular plane of incidence which contains the local surface normal. It will be shown that the specular plane of incidence and the PFR at a pixel can be determined from the same transmitted radiance information in multiple images taken through a polarizer in front of the camera sensor at different orientations. The PFR, which determines the polarization state of the specular component of reflection, can be computed by this method on "hybrid" surfaces which have significant diffuse reflection as well as specular reflection. By taking multiple images at different polarizer orientations, it is shown that the polarization state of the diffuse component of reflection can be separated out from the polarization state of the specular component of reflection.

For most specular angles of incidence (i.e., apart from 0° and 90° specular angle of incidence) the PFR is greater than 1.0 for most surface materials. This means that the polarization state of the specular component of reflection is distinct from the polarization state of the diffuse component of reflection, which is assumed to be completely unpolarized. The "Fresnel reflectance model" implies two linear independent equations, when the PFR is not 1.0, in the variables $I_d$ and $I_s$ which represent the diffuse and specular reflection component magnitudes, respectively. Determination of the PFR enables these two linearly independent equations to be solved, thus quantitatively separating diffuse and specular components of reflection.

Determination of the PFR at a pixel corresponding to an object point can classify the material that the object is made of at that point, as dielectric or metal. Assuming a specular phase angle between 80° and 140° (i.e., a specular angle of incidence between 40° and 70°) a PFR of 3.0 and greater at a pixel is indicative of dielectric material, while a PFR less than 2.0 is indicative of a metal. A PFR between 2.0 and 3.0 is indeterminate. It could indicate a semi-conductor, or a metal coated with a translucent dielectric (such as on printed circuit boards).

DETAILED DESCRIPTION OF PREFERRED EMBODIMENTS

The invention is based upon a simple model of reflection, termed the "Fresnel reflectance model", which expresses how polarization is incorporated into the radiometric model. Assume that the reflected radiance from a given object point is given by $$I_d + I_s$$

where $I_d$ and $I_s$ are the reflected radiance magnitudes of the diffuse and specular components of reflection, respectively. After the reflected radiance has been transmitted through a linear polarizer oriented at angle $\theta$ relative to the specular plane of incidence, the Fresnel reflectance model states that the transmitted radiance, $k_\theta$, is proportional to $$\frac{1}{2} I_d + \frac{F_{\parallel} \cos^2\theta + F_{\perp}\sin^2\theta}{F_{\parallel} + F_{\perp}} I_s.$$

Expressing the polarization Fresnel ratio (PFR) as $q = F_{\perp}/F_{\parallel}$, the expression for $k_\theta$ is equivalently proportional to $$\frac{1}{2} I_d + \frac{\cos^2\theta + q\sin^2\theta}{1 + q} I_s = \frac{1}{2} I_d + \frac{1 + (q-1)\sin^2\theta}{1 + q} I_s. \quad (1)$$

Figure 1A:
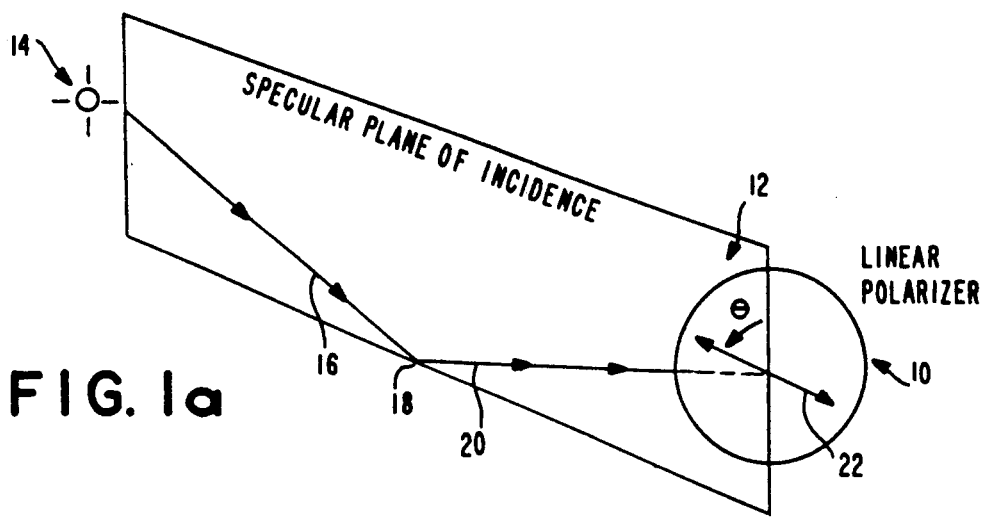
FIG. 1a shows the definition of the orientation of a polarizer at angle, $\theta$, relative to the specular plane of incidence.
Figure 1B:
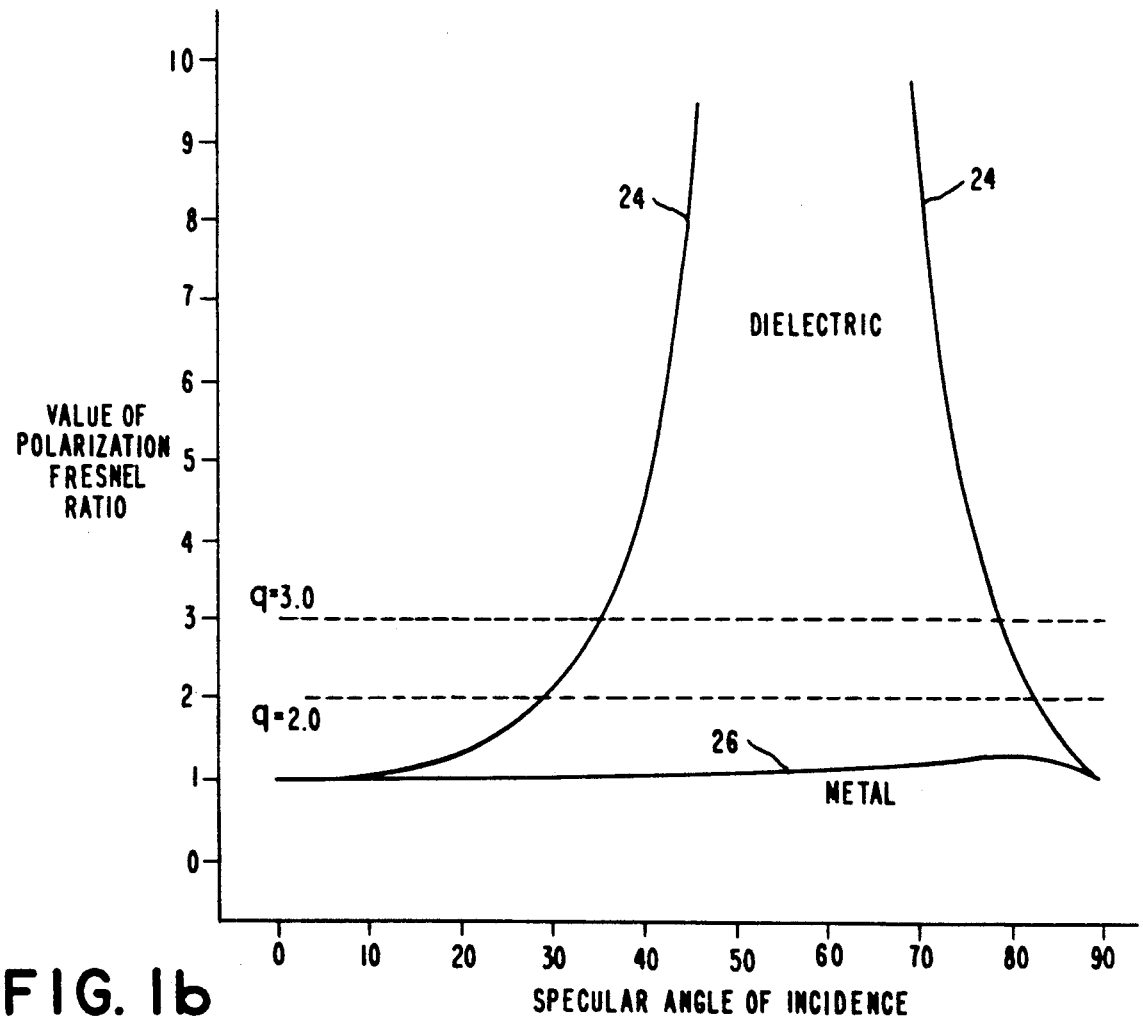
FIG. 1b shows the PFR typical of a dielectric and a metal as a function of specular angle of incidence.

FIG. 1a shows the orientation of a linear polarizer 10, oriented at angle, $\theta$, counterclockwise to the specular plane of incidence 12 for a specularly reflecting light ray from a lighting element 14, which may be part of an extended source. The light ray 16 strikes a point of incidence 18 on the surface of an object to be characterized, and the reflected ray 20 is intercepted by the polarizer 10. The polarizer has a plane of polarization 22, for example FIG. 1b shows a PFR curve 24 as a function of specular angle of incidence for a dielectric material with index of refraction n=1.7, and a PFR curve 26 for a metal material in this case; aluminum with index of refraction n=0.82 k=5.99. FIG. 1b shows that there is a definite relationship between the PFR and the specular angle of incidence. As can be seen, the determination of the specular angle of incidence from the PFR is more accurate for a dielectric than for a metal, due to the relative flatness of the metal PFR curve. These curves are very typical of PFRs for dielectrics and metals, respectively. As can be seen the PFR is always greater than or equal to 1.0.

Figure 1C:
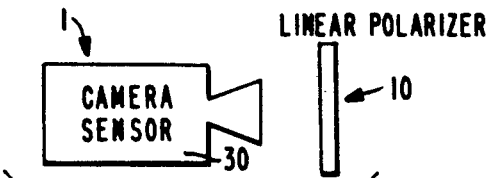
FIG. 1c shows the relationship of a polarizer and camera.

FIG. 1c illustrates the relationship between the polarizer 10 and a sensor 30, which may be a camera having an array of light-sensitive pixels for receiving polarized components of the reflected light after the light has passed through the polarizer. The component of light recieved by camera 30 will have an intensity which depends upon the angle $\theta$.

Figure 2A:
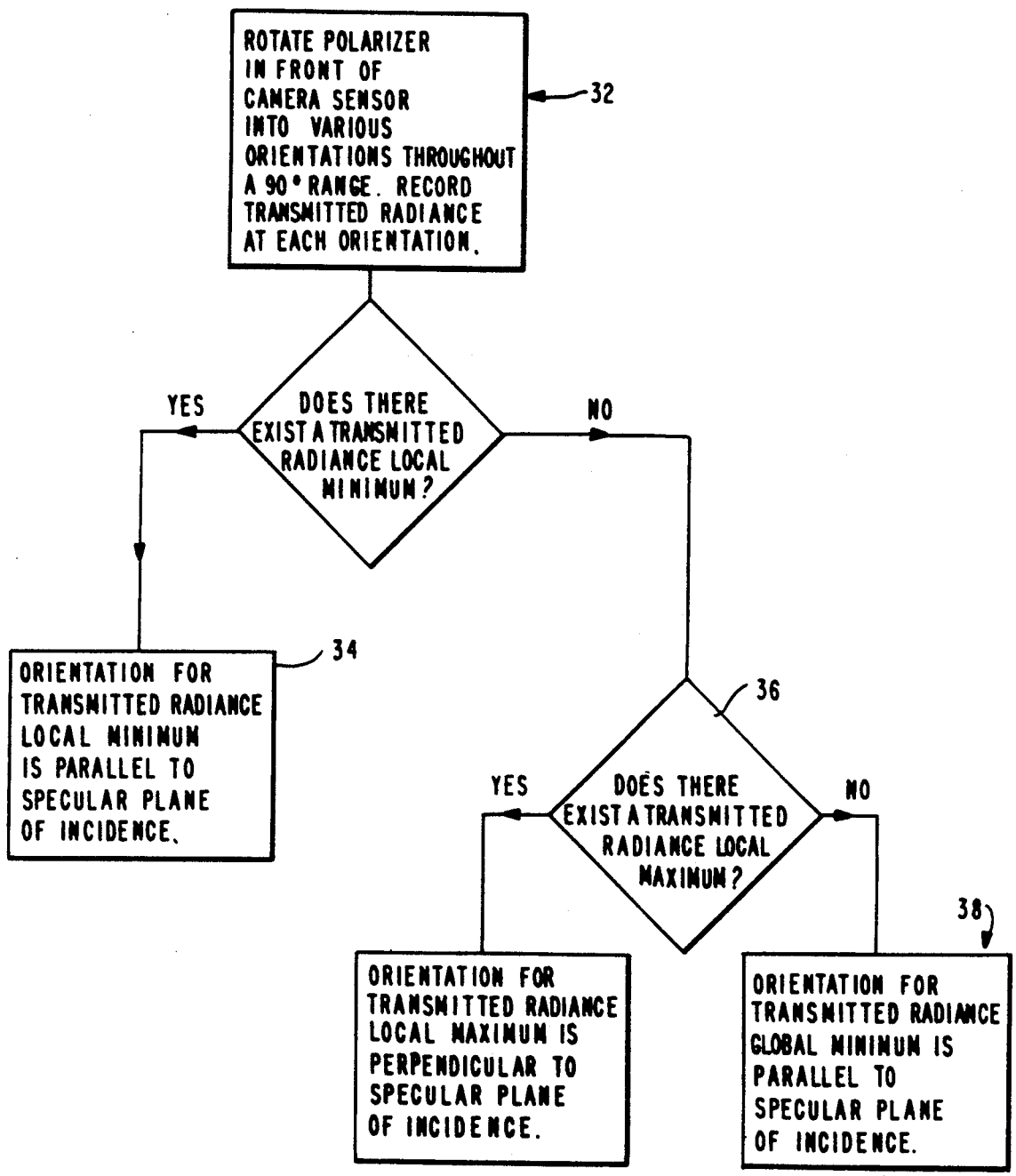
FIG. 2a shows a flow diagram of determination of orientation of the specular plane of incidence at a pixel corresponding to an object point. This technique uses transmitted radiance extrema through the polarizer as a function of polarizer orientation.
Figure 2B:
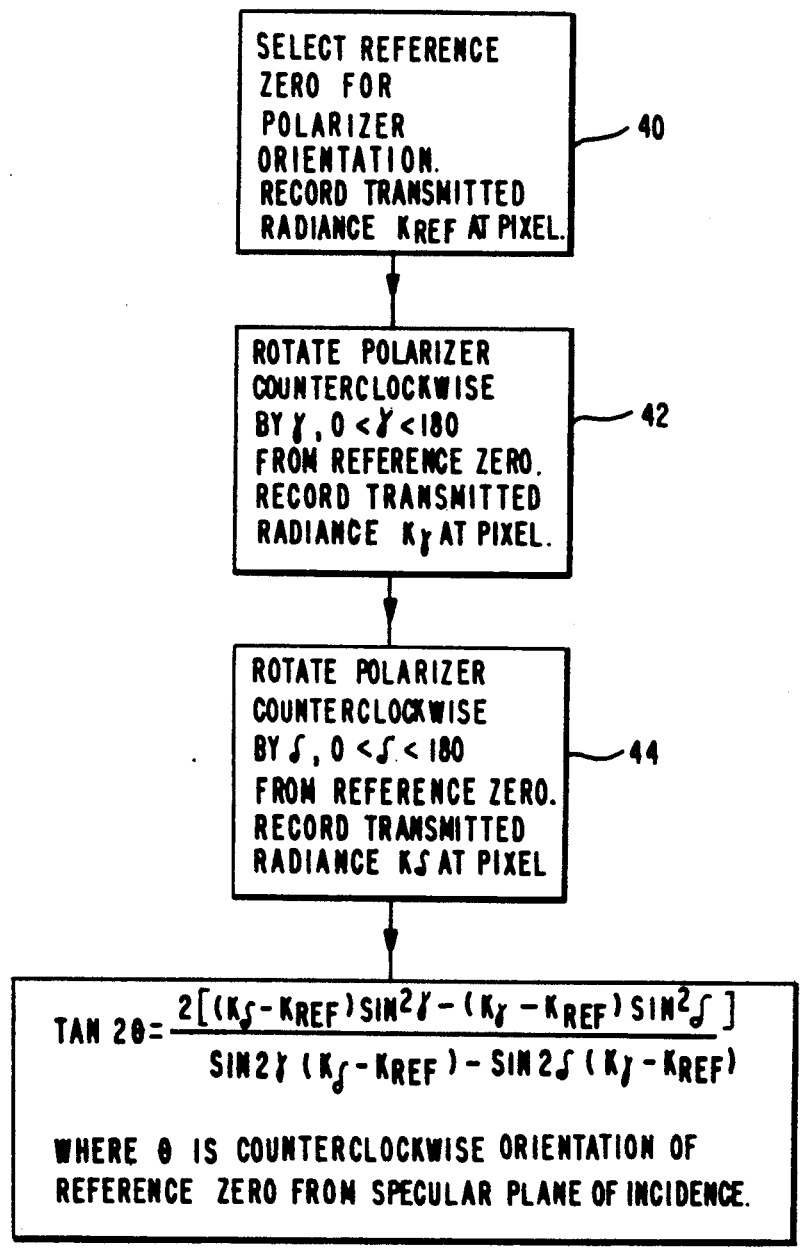
FIG. 2b shows a flow diagram of determination of orientation of the specular plane of incidence at a pixel corresponding to an object point. This technique uses transmitted radiance from three polarizer orientations.

FIG. 2a and FIG. 2b show flow diagrams for determination of polarizer orientation relative to the specular plane of incidence at a given pixel, in the image plane of the camera sensor, corresponding to an object point. Referring to FIG. 1c, the polarizer 10 is located in front of the camera sensor 30. According to equation 1, as the polarizer is oriented parallel to the specular plane of incidence (i.e., $\theta = 0$) the transmitted radiance should reach a minimum. According to equation 1, as the polarizer is oriented perpendicular to the specular plane of incidence (i.e., $\theta = 90°$), the transmitted radiance should reach a maximum. Box 32 in FIG. 2a shows that a search is performed with respect to the polarizer 10 in front of the camera sensor 1, spanning orientations within a 90° interval. At each angular orientation the transmitted radiance is recorded by the camera sensor and the flow diagram of FIG. 2a shows exactly what happens if a local minimum (box 34) or a local maximum (box 36) is found in transmitted radiance. If no local minimum or no local maximum is found, then this indicates that the boundaries of the 90° interval spanned by the polarizer are parallel and perpendicular, respectively, to the specular plane of incidence at the pixel. The box labeled 38 in FIG. 2a indicates that the global minimum is therefore parallel to the specular plane of incidence. For an accuracy of $\pm n^0$, multiple images with respect to at least $(90/2n)+1$ orientations of the polarizer are required within a 90° range.

FIG. 2b shows a flow diagram whereby the specular plane of incidence at each pixel corresponding to an object point can be determined from multiple images attained from only three distinct orientations of the polarizer 10 in front of the camera sensor 12. Referring again to equation 1, suppose that the polarizer is at some arbitrary unknown orientation, $\theta$, with respect to the specular plane of incidence. The transmitted radiance received at a pixel at this "reference zero" orientation is $k_{ref}$. (See box 40) Now rotate the polarizer counter-clockwise first by $\gamma$ (box 42) and then by $\delta$ (box 44) relative to this reference zero. These produce transmitted radiance values $k_\gamma$ and $k_\delta$, respectively, at the same pixel. Then using equation 1, the unknown orientation of the reference zero, $\theta$, relative to the specular plane of incidence is given by $$\tan 2\theta = \frac{2[(k_\delta - k_{ref})\sin^2\gamma - (k_\gamma - k_{ref})\sin^2\delta]}{\sin 2\gamma(k_\delta - k_{ref}) - \sin 2\delta(k_\gamma - k_{ref})}. \quad (2)$$

where $F_1$ and $F_{11}$ are the Fresnel reflection coefficients for the surface material of the object being measured, and where $\theta$ is the counterclockwise angle of orientation between the plane of polarization of the polarizer and the specular plane of incidence. The advantage of the technique in FIG. 2b, over the technique in FIG. 2a is that fewer multiple images from different polarizer orientations are used. The disadvantage is that because the specular plane of incidence can vary from pixel to pixel, a good $\delta$ and $\gamma$ for one pixel may be bad for another pixel with respect to accuracy of measurement.

Figure 3:
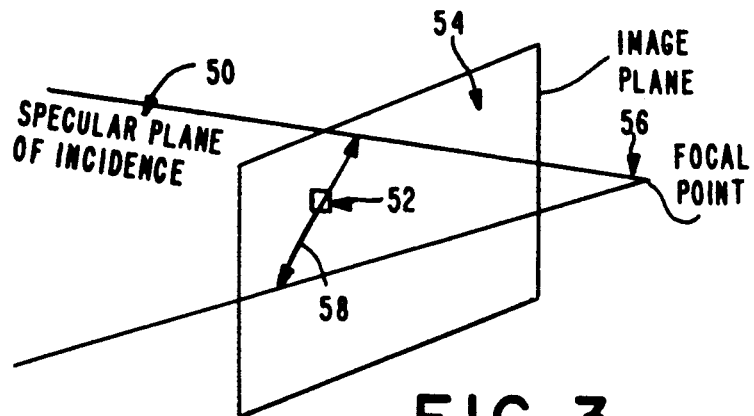
FIG. 3 shows how to determine the specular plane of incidence from known orientation at a pixel and from the relationship of this pixel to the focal point.

FIG. 3 shows the the specular plane of incidence 50 at a particular pixel 52 in the image plane 54 of the camera sensor 30 (FIG. 1e), given that the orientation of the specular plane of incidence has been determined at that pixel 52. The orientation of the specular plane of incidence 50 at the pixel 52 is determined by either of the techniques in FIGS. 2a and 2b. The specular plane of incidence with respect to this pixel passes through the focal point 56 of the camera sensor, and the orientation of the specular plane of incidence at the pixel is indicated by the line 58. The pinhole model of perspective projection is used here, and clearly the effective focal length of the camera sensor needs to be calibrated beforehand.

Figure 4A:
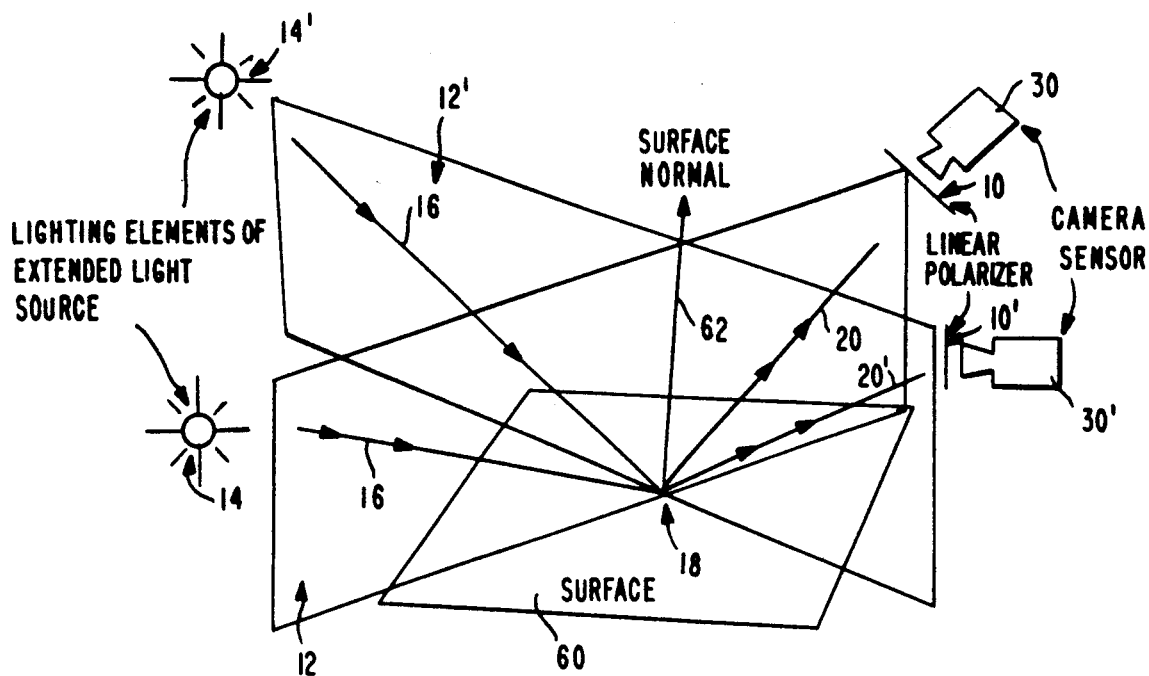
FIG. 4a shows the determination of a local surface normal from the intersection of two specular planes of incidence from corresponded pixels between 2 camera sensors.
Figure 4B:
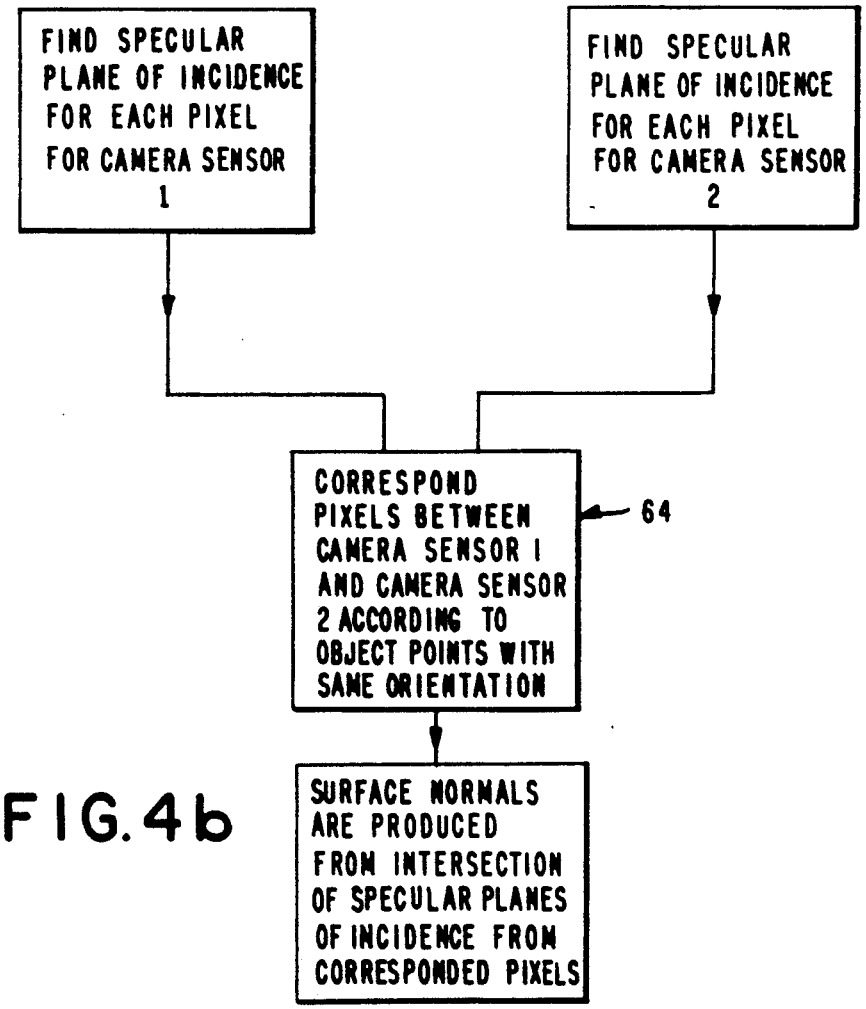
FIG. 4b shows the flow diagram for determining a local surface normal from two camera sensors.

Once the specular plane of incidence has been derived at a pixel, the surface normal at the corresponding object point is constrained to be within this plane. FIG. 4a depicts two camera sensors 30 and 30 each with polarizers 10 and 10, respectively. Lighting elements 14 and 14 are part of an extended light source which specularly reflect light off of object point 18 in a surface 60 into the camera sensors 30 and 30. At the respective pixels of camera sensors 30 and 30, receiving specular reflection from object point 18, the specular planes of incidence 12 and 12', respectively, are determined. Since the surface normal 62 at point 18 must be contained in both of these planes, the surface normal is computed from the intersection of the respective specular planes of incidence. FIG. 4b depicts a flow diagram of the two camera technique for determining local surface normals. Note that in box 64 of FIG. 4b that the correspondence between the two pixels for which the specular planes of incidence are intersected, need not require that they receive specular reflection from the same exact object point. Any two selected pixels in camera sensors 30 and 30, in FIG. 4a, which receive specular reflection from object points with the same surface orientation can correspond for the intersection of the respective specular planes of incidence will still produce the correct surface normal.

Figure 5A:
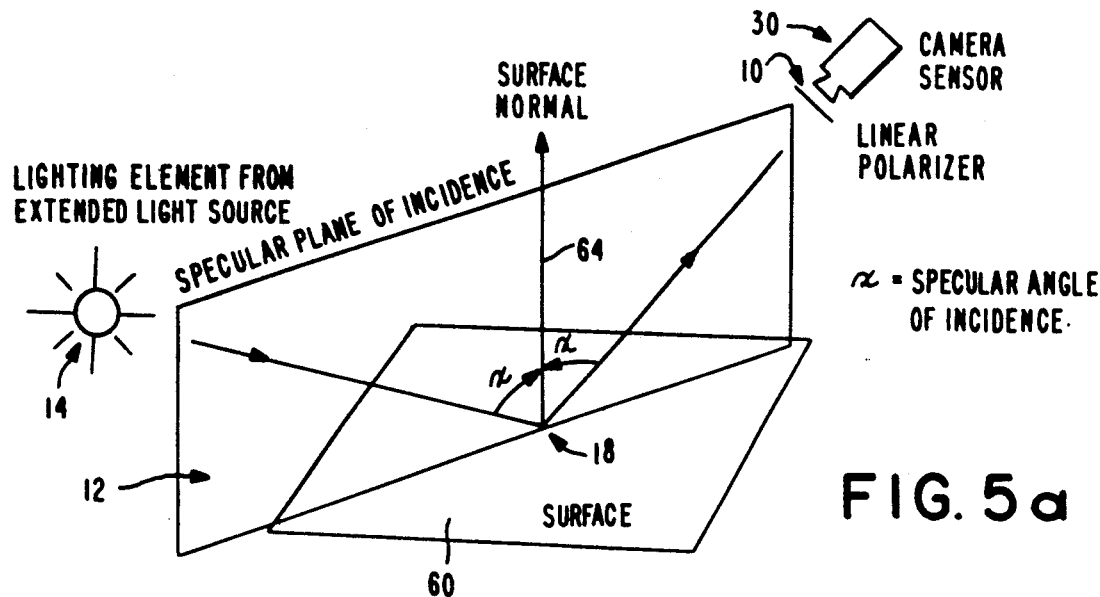
FIG. 5a shows the determination of a local surface normal from 1 camera sensor, from determination of the specular plane of incidence, and the specular angle of incidence.
Figure 5B:
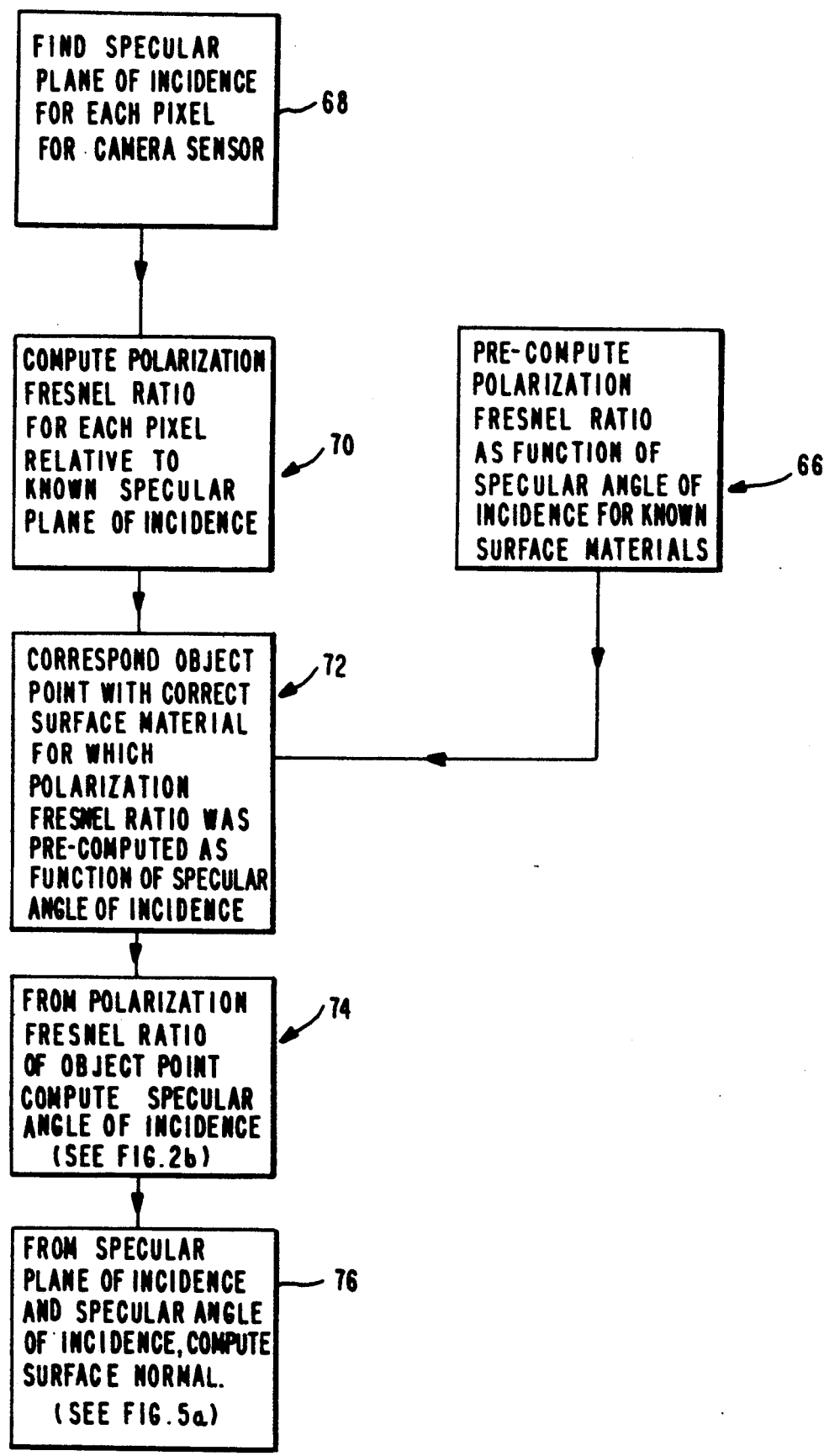
FIG. 5b shows the flow diagram for determining a local surface normal from 1 camera sensor.

FIG. 5a shows the geometry of how a surface normal is determined from a single camera sensor 30 with polarizer 10. Lighting element 14, part of an extended light 16 source, specularly reflects light from object point 18 into the camera sensor 30. The surface normal 64 is constrained to be in the specular plane of incidence 12. To uniquely determine the surface normal, the specular angle of incidence, $\psi$, needs to be determined. The technique of finding the specular angle of incidence is shown in the flow diagram of FIG. 5b, using the PFR at a selected pixel. We explain later how the PFR is determined at a pixel. The PFR is pre-determined for known surface materials (box 66) as a function of specular angle of incidence, producing curves similar to those in FIG. 1b. After finding the specular plane of incidence for each pixel in the camera sensor (box 68), the PFR of an object point, such as point 18, in the visual scene is determined, box 70, and then compared, box 72, with known materials, for which the PFR was pre-computed in box 66. Using the correct PFR curve, the PFR value of the object point is projected on the horizontal axis in FIG. 1b, to compute the specular angle of incidence, box 7.

Surface normals are determined (box 76, FIG. 5b) in FIG. 4a and FIG. 5a for all object surface points from which significant specular reflection occurs. This is what is termed as a "normal map" for the surface, whereby a surface normal is assigned to every measurable object surface point. The measurement of surface orientation from either one of the techniques describe in FIG. 4 or FIG. 5 occurs concurrently for all pixels corresponding to object points, with respect to using the same multiple images produced from corresponding polarizer orientations.

Figure 6:
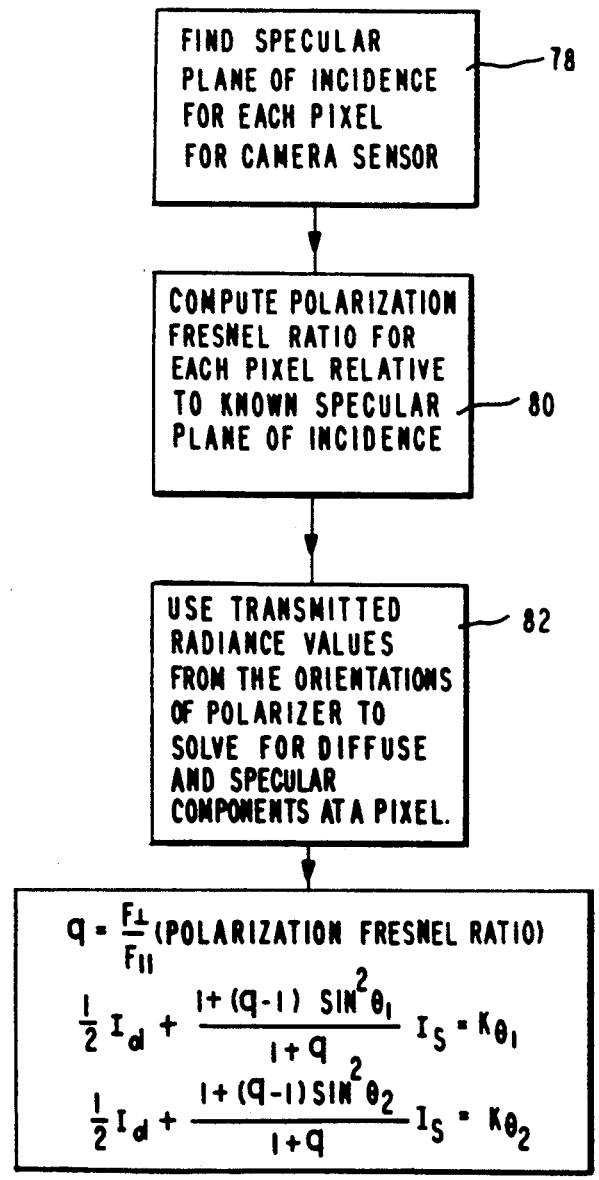
FIG. 6 shows the flow diagram for quantitative separation of reflection components.

FIG. 6 shows that if the PFR at an object point can be determined, boxes 78 and 80 then the diffuse and specular components of reflection can be separated (box 82). Equation 1 gives rise to the two linear equations in $I_d$ and $I_s$ for polarizer orientations $\theta_1$ and $\theta_2$ with respect to the specular plane of incidence;

$$\frac{1}{2} I_d + \frac{1 + (q-1)\sin^2\theta_1}{1+q} I_s = k_{\theta_1} \quad (2)$$

$$\frac{1}{2} I_d + \frac{1 + (q-1)\sin^2\theta_2}{1+q} I_s = k_{\theta_2} \quad (3)$$

where q is the PFR at the pixel. The values for $I_d$ and $I_s$ can be uniquely solved for in terms of the transmitted radiance values $k_{\theta_1}$, $k_{\theta_2}$ and q.

Figure 7:
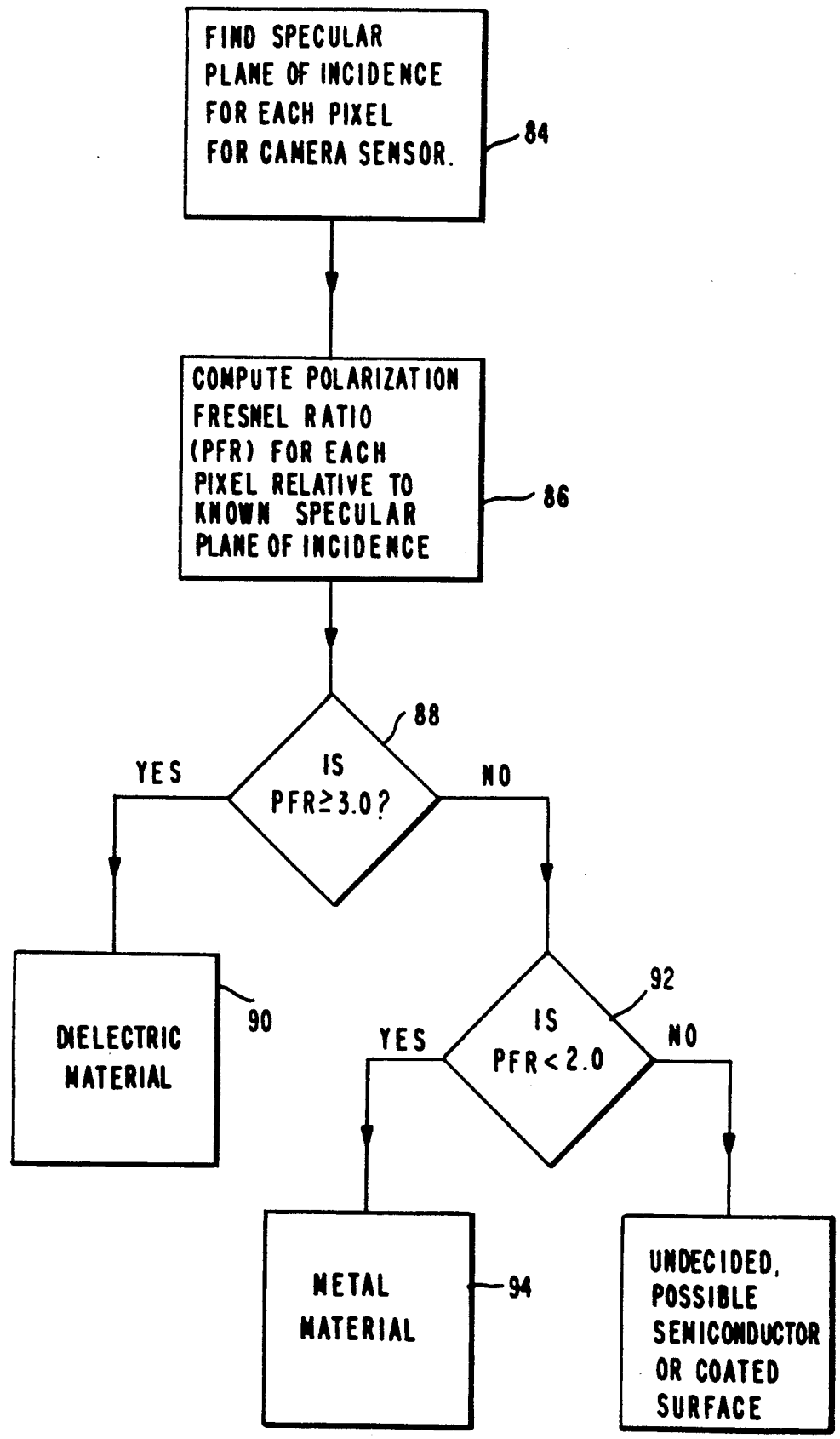
FIG. 7 shows the flow diagram for the classification of object material surfaces at pixel resolution.

FIG. 7 shows how a material surface can be classified, at a pixel, as a metal or dielectric from knowledge of the PFR at the pixel. Basically, as pictured in FIG. 1b, within the range of specular angles of incidence from 40° to 70° (specular phase angles from 80° to 140°), the PFR for a dielectric is greater than or equal to 3.0, while the PFR for a metal is somewhere between 1.0 and 2.0. Thus, after finding the specular plane of incidence for each pixel (box 84) and computing the PFR (box 86), a comparison is made at box 88 to determine whether the PFR is equal to or greater than 3.0. If so, the surface material is indicated to be a dielectric (box 90). If the PFR is less than 3.0, a comparison is made (box 92) to determine whether it is less than 2.0, and if so, the material is indicated as being a metal (box 94). If the PFR is between about 2.0 and 3.0, the material is indeterminate, and may be a semiconductor or a coated material. Thus, the PFR provides an indication of the relative electrical conductivity of the surface material.

Figure 8A:
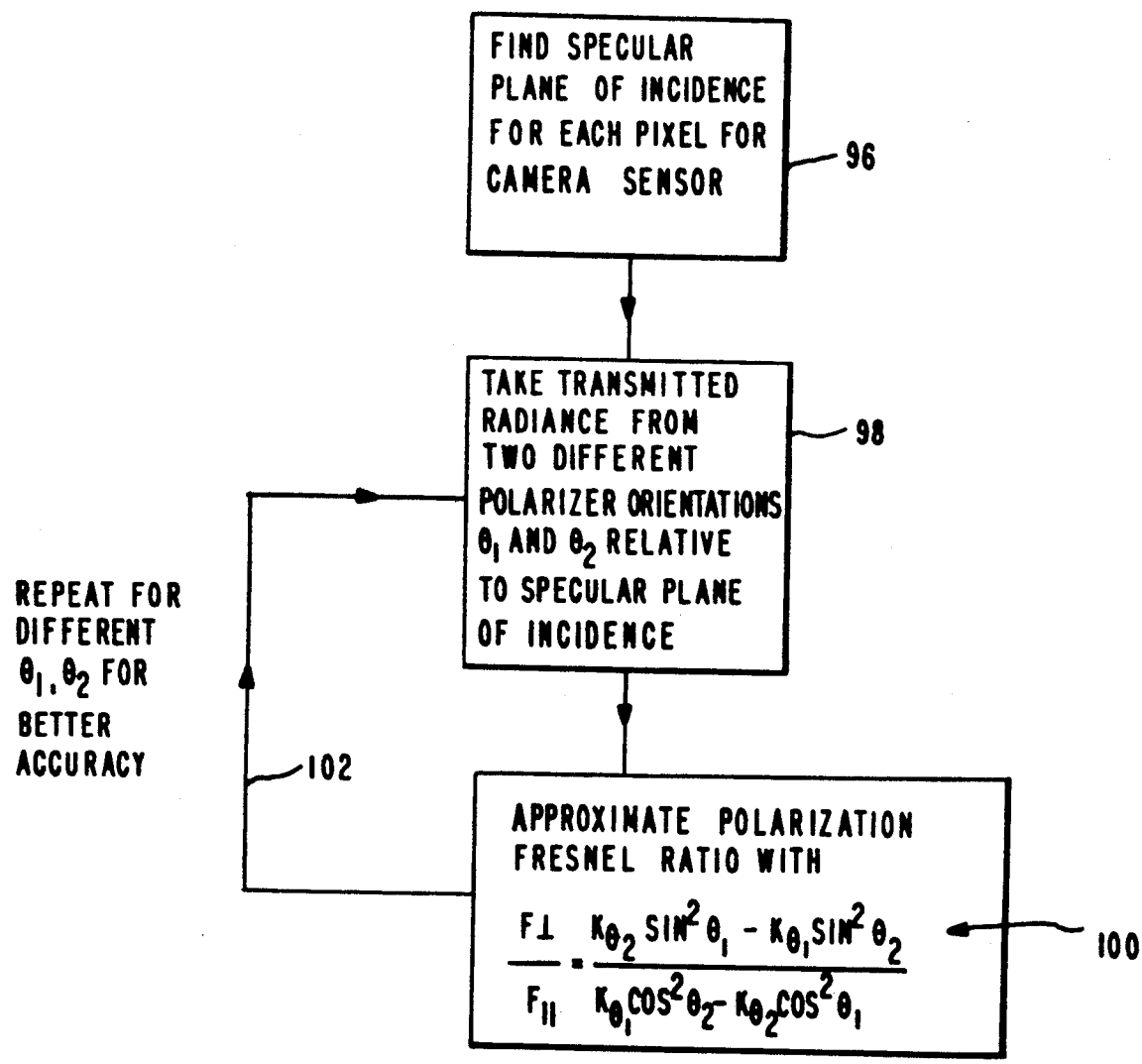
FIG. 8a shows a technique for approximating the polarization Fresnel ratio at a pixel.
Figure 8B:
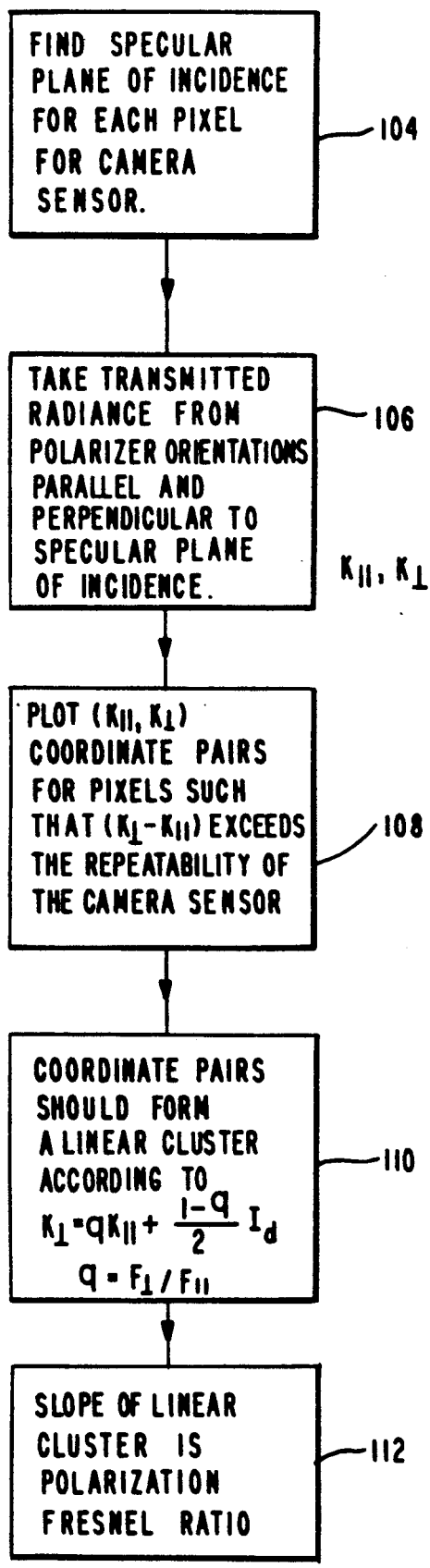
FIG. 8b shows another technique (in this case global to a group of pixels) for the determination of the polarization Fresnel ratio.

FIGS. 8a and 8b show two techniques for determining the PFR at a pixel. Again, the specular plane of incidence for each pixel is determined (box 96) and the transmitted radiance (light intensity) for two different polarization components is measured (box 98). Thereafter, the approximate PFR is determined for these measurements (box 100) and the process is repeated for different polarization components (indicated by line 102). The approximation to the PFR in FIG. 8a, (box 100) is based upon the solution for q in equations 2 and 3, in the limit as the diffuse component, $I_d$, goes to zero. If we use parallel and perpendicular polarizer orientations relative to the specular plane of incidence (i.e., $\theta_1=0°$, and $\theta_2=90°$), then the approximation to the PFR reduces to the simple expression $$\frac{k_{\theta_1}}{k_{\theta_2}}.$$

Hence in this case the PFR is approximated by the ratio of the perpendicular component of polarization, to the parallel component of polarization. Clearly, the larger the specular component of reflection is relative to the diffuse component of reflection, the better is the approximation to the PFR, PFR using the technique in FIG. 8a.

FIG. 8b illustrates another technique for determining the PFR at a pixel. After finding the specular plane of incidence for the pixel, box 104, the measured radiance for polarization components parallel to and perpendicular to the specular plane of incidence is obtained (box 106) and the coordinate pairs are plotted (box 108). The pairs form a linear cluster (box 110), and the slope of this cluster (box 112) is the PFR for the surface material. The equation used in FIG. 8b, box 110, $$k_\perp = qk_\| + \frac{1-q}{2} I_d,$$

results from equations 2 and 3 for $\theta_1=0$ and $\theta_2=90°$. This technique is only valid under the conditions that $I_d$ is constant for the polarization coordinate pairs plotted for a given object in the visual scene perceived by the camera sensor.

It is important to note that even though determination of the specular plane of incidence precedes the determination of the PFR in the flow diagrams, that both the specular plane of incidence and the PFR are derived from the same experimental data (transmitted radiance values through a polarizer at different orientations). That is the specular plane of incidence and the PFR are determined from the same front-end experimental information. This is important for speed and efficiency of the disclosed techniques.

What is claimed is:

1. Apparatus for obtaining data concerning characteristics of an object, comprising:
   a source of light;
   means directing the light onto an object, concerning which data is to be obtained, at an angle of incidence that will produce specular reflection from a region of incidence on said object;
   sensor means having an image plane located for receiving said reflected specular light, said image plane including at least one pixel, said incident light and reflected specular light intercepted by an image pixel in said image plane defining a specular plane of incidence containing the surface normal of said object at the point of incidence of said light;
   polarizing means interposed between said object and said sensor, said polarizing means producing a multiplicity of polarization components of said reflected specular light at a multiplicity of angles with respect to said specular plane; and
   means responsive to the polarization component received at said pixel for each of said angles for locating said specular plane.

2. The apparatus of claim 1, further including means for determining from said polarization components and the angle of incidence of said light the direction of said surface normal.

3. The apparatus of claim 1, wherein said polarizing means is rotatable with respect to said specular plane.

4. The apparatus of claim 3, wherein said polarizing means has a plane of polarization which is rotatable between a first position parallel to said specular plane and a second position perpendicular to said specular plane.

5. The apparatus of claim 1, wherein said polarizing means produces a multiplicity of polarization components each having a radiance corresponding to the angle of the polarizing means with respect to said specular plane, and wherein said means responsive to polarization components is responsive to a minimum radiance to locate the orientation of said specular plane.

6. The apparatus of claim 5, wherein said polarizing means has a plane of polarization which is rotatable between a first position parallel to said specular plane and a second position perpendicular to said specular plane to produce said multiplicity of polarization components.

7. The apparatus of claim 6, wherein said means responsive to said radiation components is responsive to maximum and minimum radiance for determining the orientation of surface normals at said region of incidence on said object, for classifying the relative conductivity of the material of said object at the said region of incidence, and for separating diffuse and specular components of reflection.

8. A method for obtaining data concerning the characteristics of an object surface comprising:
   directing light from a source toward an object surface to produce specular reflection from an object point on said surface;
   directing said specular reflection through a polarizer to an image plane;
   measuring the intensity of light received by a selected pixel on said image plane;
   incrementally rotating said polarizer through a series of angles with respect to a specular plane of incidence which includes said incident light, said reflected specular light, said object point and said selected pixel;
   measuring the intensity of the light received by said pixel for each incremental position of said polarizer; and
   determining therefrom the orientation of said specular plane of incidence.

9. The method of claim 8, further including determining from said measured intensity of said light incident on said object point the polarization Fresnel ratio for said object point;

determining from said ratio the angle of incidence of light on said object point; and determining from said angle of incidence the surface normal at said object point.

10. The method of claim 8, further including:

determining from said measured intensity of said light incident on said object point the polarization Fresnel ratio for said object point at said pixel;

comparing the polarization Fresnel ratio for said object point with a known polarization Fresnel ratio determined as a function of the specular angle of incidence of light on a known object surface material; and determining from the polarization Fresnel ratio of an object point the specular angle of incidence.

11. The method of claim 8, further including:

determining from said measured intensity of said light incident on said object point the polarization Fresnel ratio for said object point; and separating diffuse and specular components of light reflected from said object point.

12. The method of claim 8, further including:

determining from said measured intensity of said light incident on said object point the polarization Fresnel ratio for said object point; and classifying the material of said surface according to relative electrical conductivity from said polarization Fresnel ratio.

13. The method of claim 12, wherein the step of directing light from a source to an object surface includes directing the light at an angle of incidence of between about 40° and about 70°, and wherein the material of said surface is classifiable as a dielectric for a polarization Fresnel ratio greater than about 3.0, and as a metal for polarization Fresnel ratio of between about 1.0 and about 2.0.

14. The method of claim 8, further including:

determining from said measured intensity of said light incident on said object point the polarization Fresnel ratio for said object point for said selected pixel; and repeating for each pixel of said image plane the measurements of light intensity and the determination of the polarization Fresnel ratio for each incremental position of said polarizer with respect to the plane of incidence for each pixel.

15. The method of claim 14 further including:

comparing the polarization Fresnel ratios for each pixel with predetermined polarization Fresnel ratios for known surfaces and known angles of incidence of light on such known surfaces;

determining from the comparison of measured and known polarization Fresnel ratios for each pixel the corresponding specular angle of incidence of said light; and determining from the specular angle of incidence and the orientation of the specular plane of incidence for each pixel the surface normal at the corresponding object point.

16. Apparatus for obtaining data concerning the shape of the surface of an object, comprising: first and second spaced light sources;

means directing light from said first and second sources onto the surface of an object, concerning which data is to be obtained, at angles of incidence that will produce specular reflection from a common region of incidence on said surface;

a first sensor having an image plane including at least one pixel located for receiving reflected specular light from said first light source;

a second sensor having an image plane including at least one pixel located for receiving reflected specular light from said second light source;

first polarizing means located between said first light source and said first sensor for producing a first multiplicity of polarization components of reflected specular light from said first light source, the radiance of said components varying with the angle of polarization for each said first polarization component with respect to a first specular plane of incidence which includes said first light source, said first sensor, and said common region of incidence;

second polarizing means located between said second light source and said second sensor for producing a second multiplicity of polarization components of reflected specular light from said second light source, the radiance of said second components varying with the angle of polarization for each said second polarization component with respect to a second specular plane of incidence which includes said second light source, said second sensor, and said common region of incidence, said first and second specular planes intersecting at said common region of incidence to define a common surface normal; and means responsive to the radiance of said first and second polarization components received at said first and second sensors, respectively, for locating the orientation of said first and second specular planes with respect to the surface of said object, to thereby locate the surface normal at said common region of incidence.

17. The apparatus of claim 16, wherein each of said first and second polarization means has a plane of polarization which is rotatable between a first position which produces a maximum polarization component radiance, and a second position which provides a minimum polarization component radiance to thereby produce said multiplicity of polarization components.

18. The apparatus of claim 17, wherein said means responsive to said first and second polarization components received at said first and second sensors, respectfully, is responsive to one of (a) said maximum polarization component radiance, (b) said minimum polarization component radiance, and (c) both said maximum and said minimum polarization component radiance for determining said orientation of said surface normal, for classifying the relative conductivity of the material of said object at said region of incidence, and for separating diffuse and specular components of reflection.

19. A method of obtaining data concerning an object surface, comprising:

directing light toward an object surface to produce specular reflection from at least one region of light incidence on the surface;

directing specular reflections from said surface through polarizing means to corresponding sensor means to obtain a multiplicity of polarization components of said specular reflections;

measuring the intensity of the polarization components received by selected sensor means;

determining the maximum polarization component intensity for light reflected from a selected point of incidence on said surface;

determining the minimum polarization component intensity for light reflected from the selected point of incidence on said surface; and determining therefrom the orientation of the specular plane of incidence for the selected point of incidence.

20. The method of claim 19, further including repetitively determining the orientation of surface normals at selected points of incidence on said surface to establish surface shape, classifying the relative electrical conductivity of the object surface, and separating diffuse and specular components of reflection.

* * * * *